(12) United States Patent
Stryker et al.

(10) Patent No.: US 9,138,115 B2
(45) Date of Patent: Sep. 22, 2015

(54) CLEANING SYSTEM AND EQUIPMENT THEREFOR

(71) Applicant: STRYKER CORPORATION, Kalamazoo, MI (US)

(72) Inventors: Martin W. Stryker, Kalamazoo, MI (US); Thomas William Granzow, Plainwell, MI (US); Michael Nellenbach, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 147 days.

(21) Appl. No.: 13/672,974

(22) Filed: Nov. 9, 2012

(65) Prior Publication Data
US 2013/0117959 A1    May 16, 2013

Related U.S. Application Data

(60) Provisional application No. 61/558,190, filed on Nov. 10, 2011.

(51) Int. Cl.
*A47L 5/00* (2006.01)
*A47L 9/00* (2006.01)
*B08B 3/02* (2006.01)
*A61L 2/10* (2006.01)

(52) U.S. Cl.
CPC . *A47L 9/00* (2013.01); *B08B 3/026* (2013.01); *A61L 2/10* (2013.01); *A61L 2202/17* (2013.01)

(58) Field of Classification Search
USPC ......... 15/339, 347, 350, 353, DIG. 8; 55/429, 55/485, 486, DIG. 3
See application file for complete search history.

(56) References Cited

U.S. PATENT DOCUMENTS

| 3,975,790 | A  | * | 8/1976 | Patterson | 15/339 |
| 6,968,595 | B2 | * | 11/2005 | Oh et al. | 15/339 |
| 7,530,140 | B2 | * | 5/2009 | Makarov et al. | 15/339 |
| 7,610,652 | B2 | * | 11/2009 | Seo et al. | 15/347 |
| 7,891,046 | B2 | * | 2/2011 | Field et al. | 15/320 |
| 8,029,739 | B2 | * | 10/2011 | Field et al. | 422/292 |
| 2009/0020135 | A1 | | 1/2009 | Adams | |
| 2009/0120460 | A1 | | 5/2009 | Hekman et al. | |
| 2009/0301521 | A1 | | 12/2009 | Field | |

FOREIGN PATENT DOCUMENTS

| DE | 10 2011 010355 A1 | 8/2012 |
| JP | 08-131522 | 5/1996 |
| JP | 2006-043444 | 2/2006 |
| JP | 2007-054352 | 3/2007 |

(Continued)

OTHER PUBLICATIONS

PCT International Search Report for Application No. PCT/US2012/064353 filed Mar. 29, 2013.

(Continued)

*Primary Examiner* — Dung Van Nguyen
(74) *Attorney, Agent, or Firm* — Warner Norcross & Judd LLP (57) ABSTRACT

A cleaning system includes a housing with a reservoir for holding waste, with the reservoir in fluid communication with a suction line, a pumping station for receiving waste from the reservoir, and a cleaning component for cleaning one or more surfaces on the housing or the station either automatically or based on an actuation signal input by a user.

15 Claims, 7 Drawing Sheets

(56) References Cited

FOREIGN PATENT DOCUMENTS

| KR | 20-0161824 | 1/1999 |
| KR | 10-2007-0012109 | 1/2007 |

OTHER PUBLICATIONS

PCT International Written Opinion for Application No. PCT/US2012/064353 filed Mar. 29, 2013.

* cited by examiner

CLEANING SYSTEM AND EQUIPMENT THEREFOR

This application claims the benefit of U.S. provisional application, entitled CLEANING SYSTEM AND EQUIPMENT THEREFOR, Ser. No. 61/558,190, filed Nov. 10, 2011, which is hereby incorporated by reference in its entirety.

TECHNICAL FIELD AND BACKGROUND OF THE INVENTION

The present invention generally relates to a cleaning system and, further, to a cleaning and disposal system for collecting and disposing of waste, which is especially suitable for use in a healthcare facility, such as a hospital.

A continued concern for most healthcare facilities is infection control. While great strides have been made with equipment and cleaning solutions that, when properly used, can effectively clean a variety of surfaces found in healthcare facilities, quite often the equipment or solutions are not properly used and, further, may lead to cross-contamination.

SUMMARY OF THE INVENTION

Accordingly, the present invention provides a cleaning system with a cleaning apparatus that can be used for cleaning and disinfecting equipment, flooring, and walls in a variety of healthcare settings and which minimizes, if not eliminates, cross-contamination by incorporating one or more self-cleaning components.

In one form of the invention, a cleaning apparatus includes a self-cleaning system that cleans either the exterior surface or interior surface of the apparatus, either automatically or based on an actuation signal input by a user.

For example, the cleaning apparatus may have one or more UV lights incorporated thereon or therein that when powered clean one or more surfaces of the apparatus. In one aspect, the cleaning apparatus include floor bearing assemblies, such as casters, which have one or more UV light to wash the floor engaging portion with UV light.

In another aspect, the cleaning apparatus may include a dispensing receptacle for storing cleaning fluid, such as liquids, foam, and fluidized powders that have cleaning chemicals incorporated therein or simple have cleaning properties, such an ionized water.

In a further aspect, the cleaning apparatus may incorporate an ionization system, for example, a system that charges the cleaning fluid so that it becomes ionized. For example, the cleaning apparatus may include an anode across which the cleaning fluid flows, which ionizes the fluid. The anode may be located in the receptacle or in the discharge line of the receptacle.

In another aspect, the cleaning apparatus includes a waste receptacle for storing waste. For example, the waste receptacle is fluid communication with a suction line for suctioning waste and receipt into the waste receptacle. Further, the cleaning apparatus may be adapted to dock at a docking station where the waste in the waste receptacle may be removed.

In another aspect, the docking station may comprise a pumping station.

In yet another aspect, the waste receptacle and the dispensing receptacle share a common port, the common port being adapted to switch between a suction mode and a dispensing mode. For example, the waste receptacle and the dispensing receptacle are each in fluid communication with the common port through one or more conduits, each conduit having a valve selectively opened to control the mode of operation of the common port. In a further aspect, the cleaning apparatus includes a controller to control the valves and further a user interface to allow a user to provide input signals to the controller.

According to another aspect, the cleaning apparatus includes compartment for storing one or more accessories therein, wherein the compartment is adapted to self-clean and/or clean the accessories therein. For example, the compartment may incorporate therein UV lights that when powered clean the compartment and/or the accessories therein.

In another form of the invention, a cleaning system includes a housing with a receptacle for holding waste, the receptacle in fluid communication with a suction line, and a docking station for receiving waste from the receptacle, wherein the housing or the docking station is self-cleaning.

For example, one or more UV lights may be located at the docking station, which when powered wash the docking station and/or housing with UV light to clean the docking station and/or housing.

In a further aspect, the system includes a dispensing unit for dispensing replacement accessories. The dispensing unit may be configured to monitor the quantity and type of accessories dispensed there from, for example, for inventory management and/or for charging to an account, such as a patient account.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENT

Figure 1:
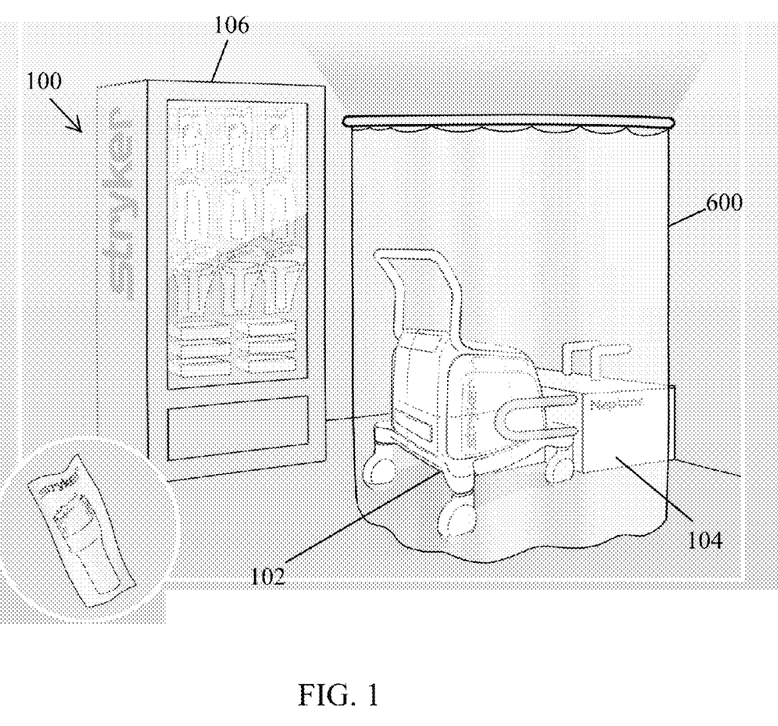
FIG. 1 is a perspective view of a cleaning apparatus of the present invention docked in a docking apparatus for emptying the apparatus of waste fluids stored therein with a UV enclosure, including a dispensing unit for dispensing replacement tip, nozzles, hoses, or the like that can be used in conjunction with the apparatus.

Referring to FIG. 1, the numeral 100 generally designates a cleaning system of the present invention. Cleaning system 100 includes a mobile waste collection and dispensing apparatus 102, a docking station 104, and an optional replacement part dispensing unit or kiosk 106. The waste collection and dispensing apparatus 102 allows a caregiver to dispense cleaning fluids, including liquids, foam or fluidized powder etc, onto a surface or onto a floor for cleaning the surface or floor and, further, allows the user to thereafter collect the cleaning fluid and waste material generated during the cleaning process. As will be more fully described below, apparatus 102 is configured to store waste, including cleaning fluids that are dispensed from the apparatus and then recovered after disinfection has been completed, until such a time that a user is ready to empty and dispose of the waste material. Further, apparatus 102 may be configured to cooperate with docking station 104, which empties the waste material from apparatus 102 to a waste drum D or treatment area, thereafter allowing the collection apparatus to be optionally cleaned for further use. For details of optional features (not described herein) that may be incorporated into apparatus 102 and details of docking station 104 reference is made to U.S. Pat. No. 7,621,898 entitled MEDICAL SURGICAL WASTE COLLECTION UNIT INCLUDING WASTE CONTAINERS OF DIFFERENT STORAGE VOLUMES WITH INTER-CONTAINER TRANSFER VALVE AND INDEPENDENTLY CONTROLLED VACUUM LEVELS, which is commonly assigned to Stryker Corporation of Kalamazoo, Mich., which is incorporated by reference herein in its entirety.

Figure 2:
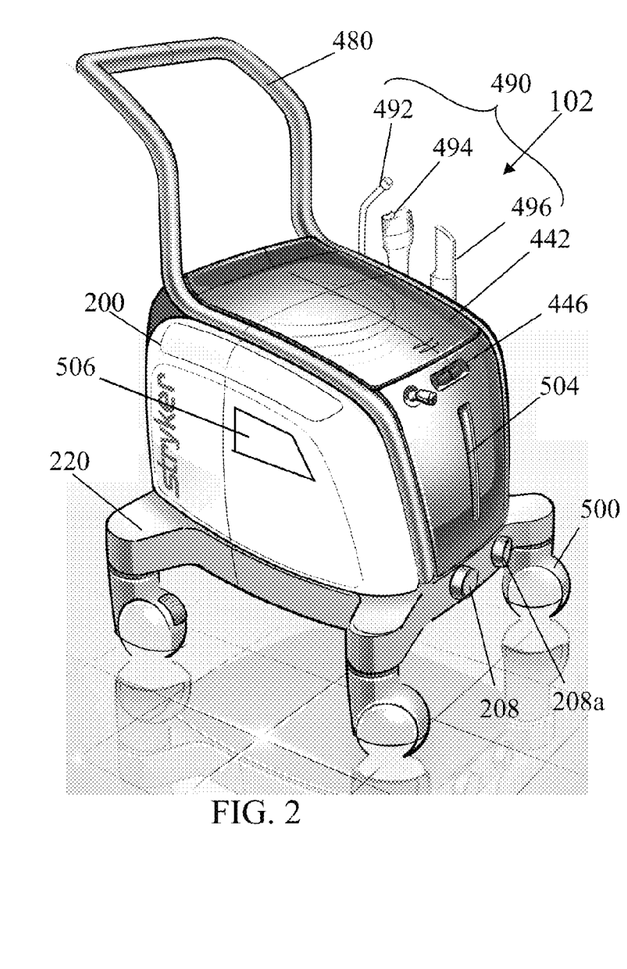
FIG. 2 is a perspective view of the cleaning apparatus of FIG. 1.
Figure 3:
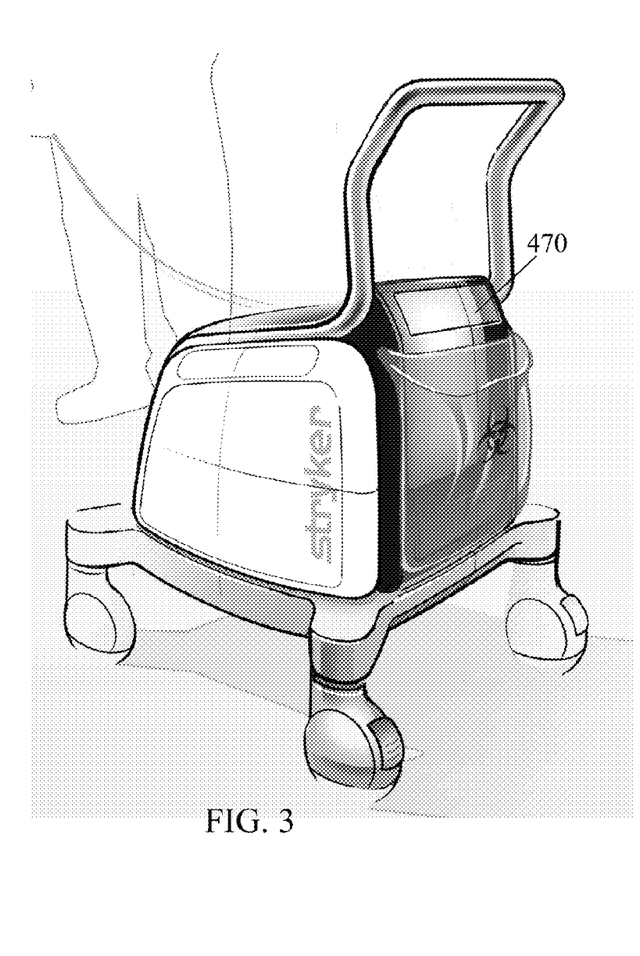
FIG. 3 is a rear perspective view of the apparatus of FIG. 2.
Figure 4:
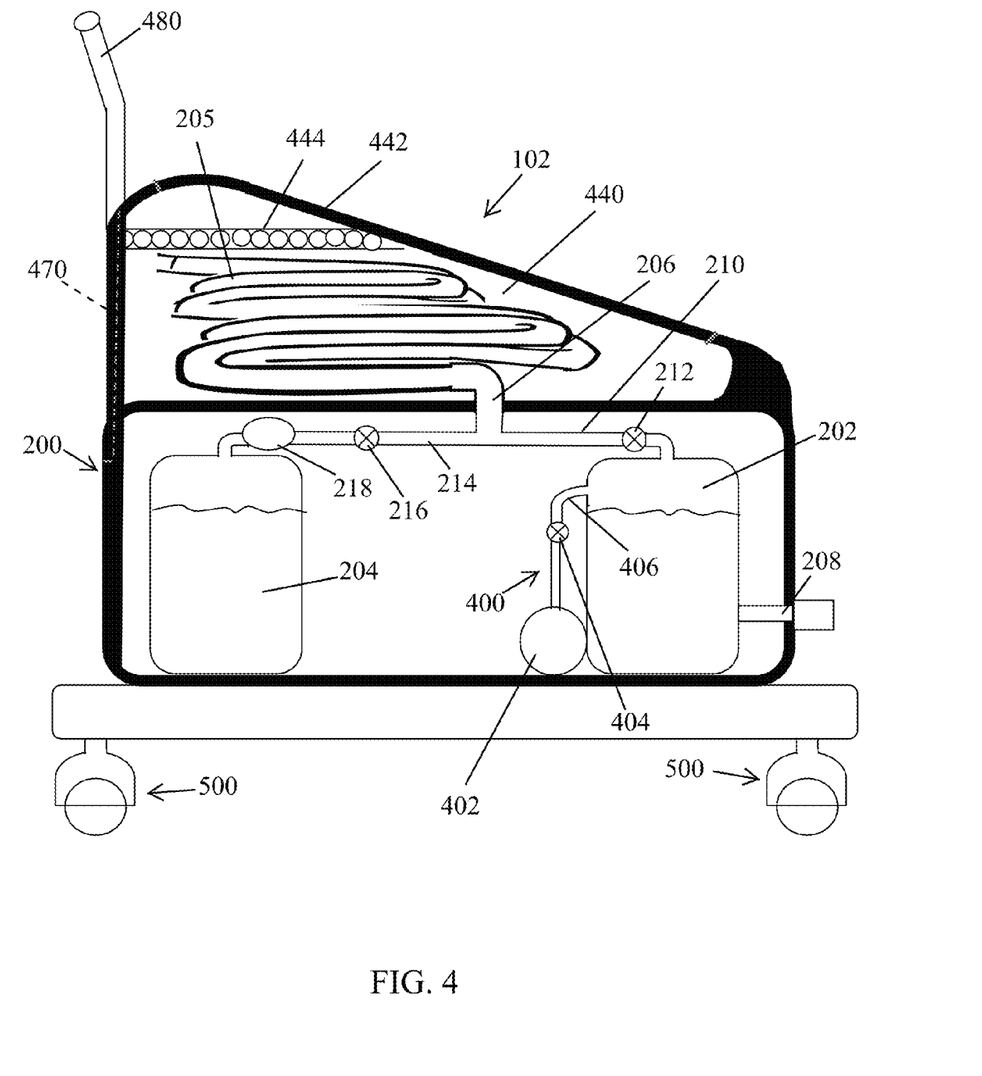
FIG. 4 is a cross-sectional view of the cleaning apparatus of FIG. 2 illustrating the internal reservoirs and conduits for moving fluids through the apparatus.

Referring to FIGS. 2-4, waste collection and dispensing apparatus 102 includes a housing 200, which includes one or more reservoirs or receptacles 202 therein for collecting and temporarily storing waste material during use. Optionally, housing 200 also includes a second reservoir or receptacle 204 therein for storing cleaning fluids, which can be dispensed from the apparatus as will be more fully described below. Alternately, receptacle 204 may be externally mounted to housing 200 or may include an external reservoir mounted to the hose described below, for holding, for example, a concentrated form of the cleaning fluid, which is then mixed with water delivered from receptacle 204, using a common venture connection. In another embodiment, apparatus 102 may comprise a cleaning apparatus with only a reservoir or receptacle therein for storing and dispensing cleaning fluids. The term "cleaning fluids" is used herein broadly and includes liquids, foam, and fluidized powders that have cleaning chemicals or simply have cleaning properties, such as ionized water.

Housing 200 may be formed from a plastic, including reinforced plastic, or a metal material or a hybrid material and may be formed from unitary body or two or more panels or body portions. Receptacles 202 and 204 may also be formed from plastic, including reinforced plastic, metal, a hybrid material, or glass. The size and shape of the housing and receptacles can be varied depending on the desired capacity of the waste collection and dispensing apparatus. Optionally, housing 200 is either mounted to or formed with a wheeled base 220 to facilitate transport of apparatus 102. Further, the base may incorporate a powered wheel or powered wheels to form a self-propelled or power assisted apparatus.

Optionally, apparatus 102 may incorporate a system to clean fluid dispensed from or waste stored therein. For example, receptacle 202 and/or 204 may incorporate an ionizing system, for example, in the form of a copper liner or anode or an electrical system, to ionize the fluid or waste held therein. For example, an electrical circuit may be provided that applies a low electric field to the fluid stored on receptacle 202 (or 204) to ionize the fluid or waste contained therein. Alternately or in addition, receptacle 202 (or 204) may incorporate an anode in the suction or discharge conduit 210 or 214 or in the receptacle itself, again to ionize the fluid as it flows to and/or from receptacle. In this manner, water can be used as the cleaning fluid. Further, the fluid system may incorporate one or more filters, as noted below, such as described in the above-referenced patent.

Receptacle 202 is in fluid communication with a port 206, which is adapted for coupling to a hose 205, which transports waste to receptacle 202 by way of a vacuum, described below. Further, receptacle 202 is in selective flow communication with a second port (outlet) at housing 200, preferably at the underside of housing 200, which is adapted for fluid communication with the docking station 104 when apparatus 102 is properly aligned (e.g. when guides 208 and 208a on the front end of housing 200 align with guides on station 104 (e.g. referred to as strike plates 1022 and receivers 1024 in the reference patent)). For details of how apparatus 102 can dock with station 104 and can remove the waste from receptacle 202, reference again is made to U.S. Pat. No. 7,621,898.

To draw the "spent" or used cleaning fluid and/or waste into receptacle 202 through hose 205 and port (inlet) 206, apparatus 102 includes a first conduit 210, with an isolation valve 212, and a vacuum circuit 400. Circuit 400 includes a vacuum pump 402 and a control valve 404, which are in fluid communication with receptacle 202 via conduit 406. Thus when pump 402 is powered, pump 402 will generate suction at port 206 and draw in used cleaning fluid and/or waste into receptacle 202. Similarly, receptacle 204 is in fluid communication with port (now an outlet) 206 via a conduit 214, with a control valve 216 and a pump 218, which selectively delivers cleaning fluid stored in receptacle 204 to hose 205 when valve 216 is opened and pump 218 is operated. In this manner, control valves 212 and 216 allow hose 205 to be switched between a dispensing line for delivering the cleaning fluid to a surface or floor to be cleaned by the user and a suction line to recover used cleaning fluid or simply to vacuum waste. However, it should be understood that separate ports may be provided, either adjacent or coaxial, with hose 205 provided with two designated channels or lumens (adjacent or coaxial)—one for suction and the other for dispensing fluid—that are in fluid communication with the respective outlets.

Further, as note above, vacuum circuit may incorporate a filter to collect and filter out debris that may be vacuumed up along with the fluid. For example, when cleaning an area such as a surgery theatre, items such as cotton balls, burrs, blades, sponges, large pieces of human tissue, etc. could be drawn into the system but which will not easily flush away with the liquid wastes. For example, the filter may be provided between port 206 and valve 212 or between valve 212 and receptacle 202. Further, housing 200 may incorporate an access door 506 at the side of the housing so that the filter may be removed for cleaning or replacement. The filter may be configured as a basket or screen which can then be lifted out or removed by way of door 506 to be disposed in an appropriate way.

Figure 5:
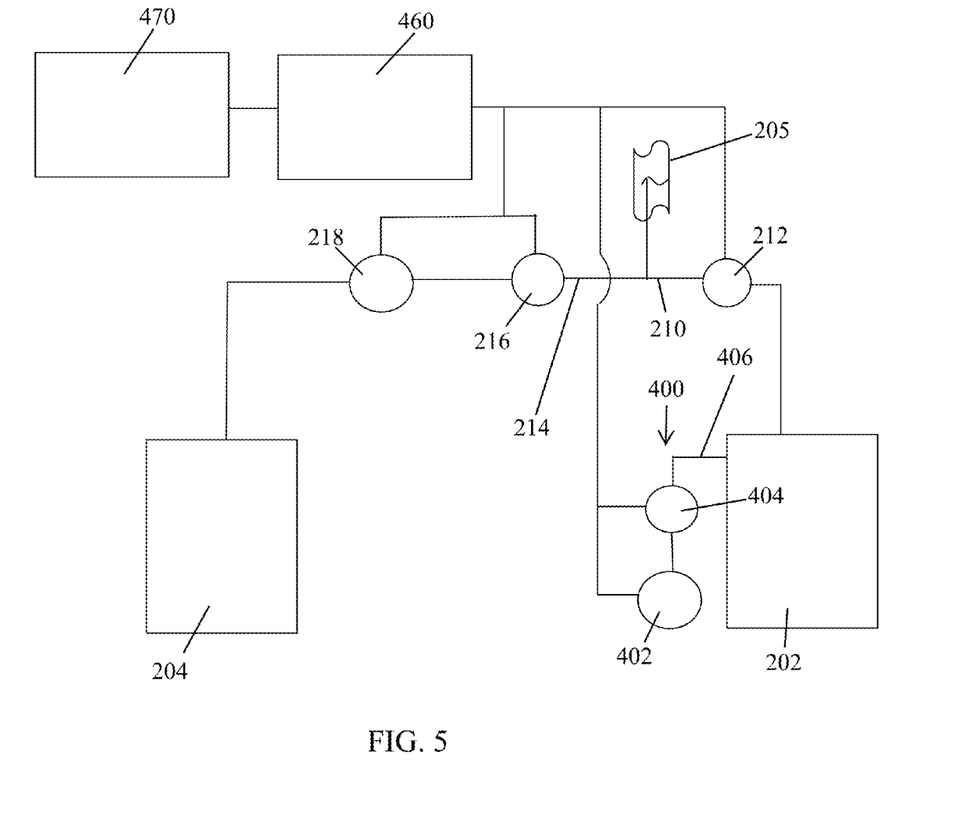
FIG. 5 is a schematic drawing of one embodiment of the control system of the apparatus of FIG. 2.

To control the mode of operation (e.g. suction mode or dispensing mode) and other powered components on apparatus 102 (e.g. ionization system described above or UV lights described below), apparatus 102 includes a controller 460, which is in communication with pumps 218 and 402 and valves 212, 216, and 404 (and ionization system described above or UV lights described below), and a user interface 470, which allows a user to power up the apparatus (as well as other components on apparatus 102) and further select the mode of operation. For example, the user interface may comprise a plurality of keys or buttons or a touch screen with an optional display. The user interface may be mounted on the housing (as shown in FIG. 3) or on the push handle 480 and may include additional buttons or touch screen areas for the other functions described above and below.

Thus, when a user wishes to dispense the cleaning fluid, the user will power up the apparatus and actuate the button or touch screen area associated with the dispensing mode, so that controller 460 will close valve 212 and open valve 216 and then energize pump 218 so that fluid contained in receptacle 204 will be dispensed through hose 205. On the other hand when user wishes to vacuum up the liquid or waste, the user will actuate the button or touch screen area associated with the vacuum mode, and controller 460 will turn off pump 218, close valve 216 and open valve 212, and then energize pump 402 to thereby convert hose 205 into a suction line, which will draw the waste and/or fluid into receptacle 202 for later disposal through the disposal outlet. The rate of suction may be controlled using valve 404, which is controlled by controller 460 and optionally by the user at the user interface.

Figure 8:
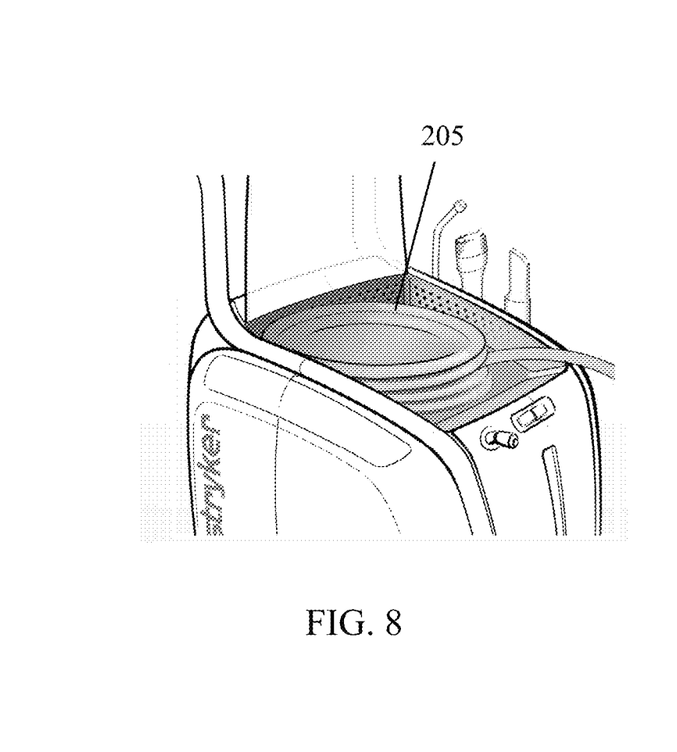
FIG. 8 is a top partial perspective view of the apparatus of FIG. 2 illustrating an upper inner compartment that stores the hose for dispensing fluid and/or for vacuuming fluid from or into the reservoirs located in the apparatus.

In the illustrated embodiment, outlet 206 is located in the upper portion of housing 200. Optionally, outlet 206 is located in an enclosed compartment 440 formed by a recess in the upper portion of housing 200 and by a cover or panel 442, which may be hinged on one end to housing 200 and latched at its other end when in a closed position. In this manner, when hose 205 is coiled, it may be stored in apparatus 102 in compartment 440. Further, cover 442 may be adapted to allow the hose to be extended from the compartment with cover in its closed position.

Referring to FIG. 4, one or more UV lights 444, such as LED UV lights, may be mounted in compartment 440, which when energized wash the hose 205 stored in compartment 440, as well as the compartment itself, with UV light to thereby clean the hose and compartment. The UV lights may be controlled by controller 460, as noted above, or may be independently energized by a toggle button or switch mounted for example to the front of the housing as shown in FIG. 2 adjacent the cover 442 of the compartment 440. Optionally, the energizing circuit (whether actuated by the controller or toggle switch) may include a timer or timing circuit to assure that the UV wash is activated for a sufficient amount of time to be effective, which could be interrupted, for example, if the cover or panel 442 was opened. Additionally, mounted adjacent the cover 442 is an optional indicator or warning 446, such as light, which indicates when the UV lights are energized so that a user will know not to open cover or panel 442 and avoid exposure of the user to the UV light. Further, the latch on the cover may be locked by an actuator, controller by controller 460 or the switch, when the UV light or lights are energized to prevent inadvertent opening of compartment. Additionally, should the latch not be properly locked and the actuator unable to lock the latch, the controller 460 or the switch may be inhibited from powering the lights.

Optionally, hose 205 may be coupled to one or more accessories 490, such as applicator tips 492, 494, and 496, for dispensing the cleaning fluid, which may be mounted in a receptacle formed in the wall of housing 200 or mounted on posts or other structures provided or formed on the housing. Optionally, accessories 490 may be made from a disposable material so that they may be removed and replaced to avoid cross-contamination. Furthermore, accessories 490 may be made from a material that can be dissolved or at least partially broken down and then vacuumed up with the waste by apparatus 102.

Figure 9:
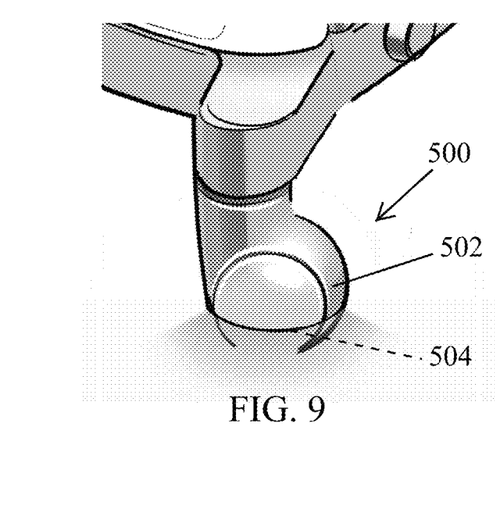
FIG. 9 is an enlarged view of one of the castors of the apparatus of FIG. 2 illustrating a UV light incorporated into the castor.

Optionally, additional UV lights may be provided in the castors or wheels 500 that support housing 210. Referring to FIG. 9, housing 200 includes wheeled base 220 with a plurality of floor bearing assemblies, such as castors 500, mounted thereto. Each castor 500 may incorporate a shroud 502 and a UV light or an array of UV lights 504, which direct UV light onto the floor engaging portion (wheels) of castors to clean the wheels when energized and further protect a user from the UV light. In this manner, when apparatus 102 is transported between locations in a hospital or another healthcare facility, the castors can be cleaned to avoid cross-contamination. Actuation of the UV lights may be controlled by a user, for example, by way of user interface 470 or a switch or button, or they may be actuated based on input from apparatus 102, for example, when one of the pumps are actuated or when apparatus 102 is simply powered on.

Figure 6:
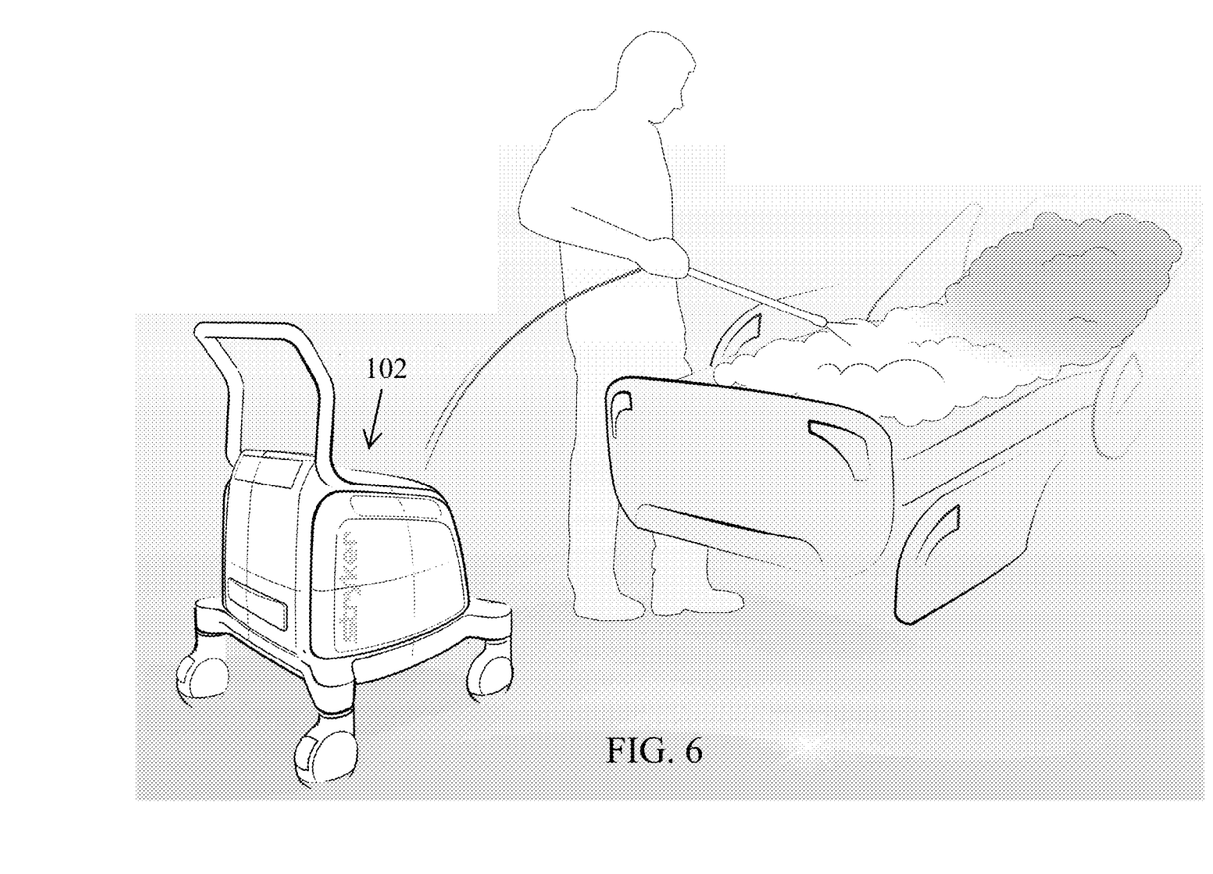
FIG. 6 is another perspective view of the apparatus of FIG. 1 illustrated showing use of the apparatus for cleaning equipment, such as a hospital bed.
Figure 7:
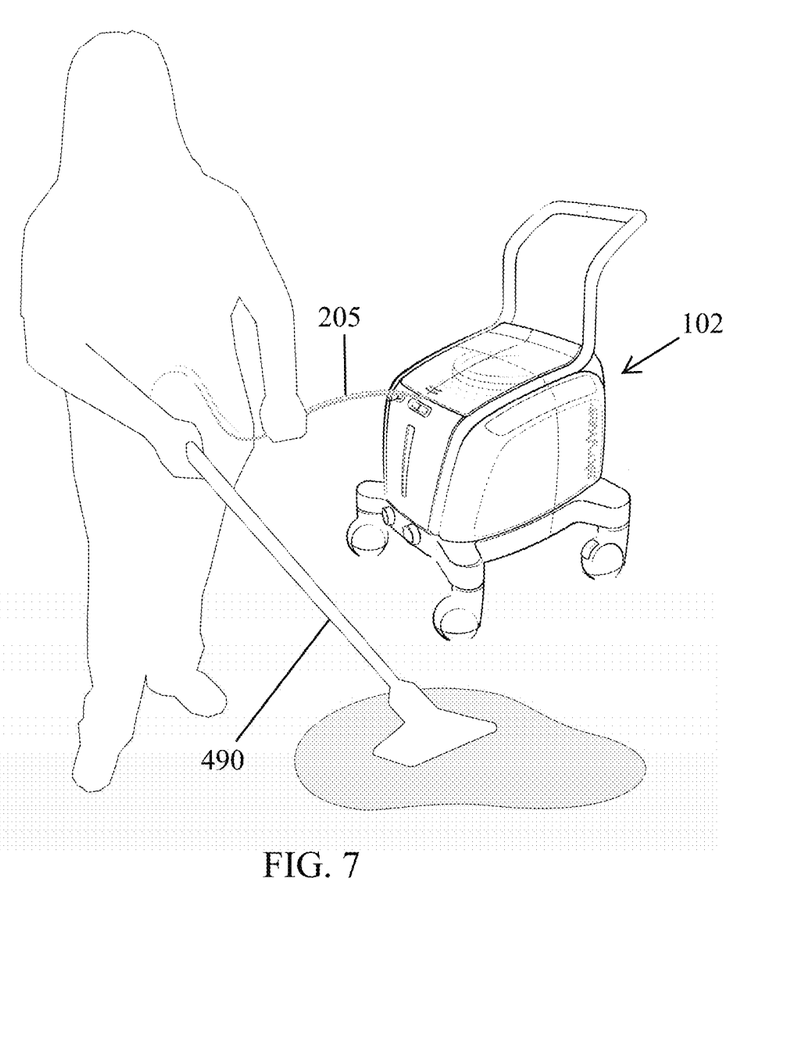
FIG. 7 is another perspective view of the apparatus of FIG. 1 illustrating the apparatus being used as a vacuum.

Referring to FIG. 6, when a user wishes to apply a spray of cleaning fluid or foam, the user may use the cleaning tip accessory 492, which may generate a dispersed or concentrated spray of a fluid flowing from hose 205. For example, a suitable cleaning fluid or foam with cleaning chemicals may include a cleaning fluid or foam that changes color after a predetermined time has passed, which indicates that the cleaning fluid or foam has cleaned the surface. For example, such cleaning fluids or foam are available under the trade name Kaboom®. In this manner, a user may spray the cleaning fluid or foam mixture onto a surface, such as a hospital mattress. Once the cleaning fluid or foam has changed color to indicate a sufficient passage of time has occurred, the user may then suction up the fluid.

Optionally, apparatus 102 may incorporate an indicator of the level of the waste receptacle and/or the cleaning fluid receptacle. In the illustrated embodiment, housing 200 incorporates in its housing wall a transparent window to allow viewing of the receptacle, which as described in the referenced application, may be formed from a clear plastic or glass. A similar window may be provided on the side or end adjacent the cleaning fluid receptacle. For example, as shown in FIG. 2, housing 200 may include an elongate opening 504, which has a transparent window. Alternately, sensors may be provided in the receptacles to provide an indication of the level of the fluid in the respective receptacle, which sensor is in communication with the controller. Controller 460, for example, may generate a signal, including a visual indicator, such as a numerical indicator or a series of LED's that are lit up to indicate the degree of fill, or an audible signal or the like.

Referring to FIG. 3, housing 210 may also incorporate one or more engagement structures to allow a bag, such as a biohazard bag, to be suspended from the housing so that, for example, when the accessories are used and need disposing of, the accessories may be deposited into the biohazard bag for proper disposal.

Referring to again to FIG. 1, when the waste collection and dispensing apparatus 102 is ready to be emptied, apparatus 102 is wheeled to the docking station 104 to mate with the docking station 104 as described in the referenced patent, which empties the waste reservoir of apparatus 102. Once the respective couplings of the apparatus 102 and docking station 104 are aligned and the waste collection apparatus and the docking station are in fluid communication, the docking station pump can then suction the waste from the receptacle 202 as noted above. As described in the referenced patent, the docking station 104 includes an off-load pump, which is disposed in the cabinet forming the docking station, and which is connected to a waste drain to pump the waste material from the waste collection apparatus 102 to the waste drain when the waste collection apparatus is docked to the docking station.

Optionally, a curtain 600 or similar barrier may be provided around apparatus 102 and docking station 104 so that apparatus 102 and docking station 104 may be cleaned using, for example, UV lights. Once apparatus 102 is docked at docking station 104, the curtain or wall may be erected or positioned to protect the user of the cleaning equipment from the UV rays generated by the UV lights. For example, the UV lights may be mounted to the ceiling above the docking station or in a frame mounted above the docking station. Optionally, as part of the cleaning system, as noted, an accessory dispensing unit 106, similar to in a vending machine, may be provided, which allows a user to select an accessory or accessories (replacement tips, hoses, filters etc) using a keypad, which is then dispensed through a door for use by the user. Dispensing unit 106 may incorporate a front glass panel to view the accessories and a tracking or inventory control software to monitor the use of the accessories and charge the use of the accessory where appropriate. For example, unit 106 may include a keypad that allows a user to enter a patient's identification number into the system so that the accessory may be charged to that patient.

According to the present invention provides a cleaning system that caregivers and housekeeping personnel to safely clean and disinfect surfaces from floors and equipment. The system provides a user friendly system that can indicate when disinfection is complete to assure greater cleanliness in the hospital or healthcare environment. The system may be used in patient transportation, such as an ambulance, in hospital rooms and surgical rooms, as well as in extended or home healthcare settings.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A cleaning apparatus comprising:
   a housing with a dispensing reservoir for holding a cleaning fluid;
   an ionization system for charging the fluid so that it becomes ionized, the ionizing system comprising a cleaning component, said cleaning component including an anode in contact with the cleaning fluid, the anode for ionizing the cleaning fluid either automatically or based on an actuation signal input by a user;
   a waste reservoir for storing waste; and
   a suction line, the waste reservoir being in fluid communication with the suction line for suctioning waste and receipt into the waste reservoir, wherein the waste reservoir and the dispensing reservoir share a common port, the common port being adapted to switch between a suction mode and a dispensing mode.

2. The cleaning apparatus according to claim 1, wherein the waste reservoir and the dispensing reservoir are each in fluid communication with the common port through one or more conduits, each conduit having a valve selectively opened or closed to control the mode of operation of the common port.

3. The cleaning apparatus according to claim 2, further comprising a controller to control the valves and further a user interface to allow a user to provide one or more input signals to the controller.

4. The cleaning apparatus according to claim 2, further comprising a compartment for storing one or more accessories therein, wherein the compartment is adapted to self-clean and/or clean the accessories therein.

5. The cleaning apparatus according to claim 4, wherein the compartment incorporates one or more UV lights that when powered clean the compartment and/or the accessories therein.

6. A cleaning system comprising a cleaning apparatus of claim 1, further comprising a pumping station for receiving waste from the reservoir.

7. The cleaning system according to claim 1, further comprising a second cleaning component operable to clean an exterior surface of the housing or the waste contained in the waste reservoir either automatically or based on an actuation signal input by a user.

8. The cleaning system according to claim 7, wherein the second cleaning component comprises one or more UV lights.

9. The cleaning system according to claim 7, wherein the housing includes floor bearing assemblies, each of the floor bearing assemblies having a floor engaging portion, the second cleaning component for cleaning at least one of the floor engaging portions.

10. The cleaning apparatus according to claim 1, wherein the anode is located in the dispensing reservoir or in a discharge line of the dispensing reservoir.

11. The cleaning apparatus according to claim 1, further comprising a second cleaning component, said second cleaning component cleaning the waste in the waste reservoir or an exterior surface of the cleaning apparatus.

12. The cleaning apparatus according to claim 11, wherein the second cleaning component is located in the waste reservoir or in a suction line of the waste reservoir.

13. The cleaning apparatus according to claim 1, wherein the second cleaning component comprises one or more UV lights.

14. The cleaning apparatus according to claim 1, wherein the cleaning apparatus is adapted to dock at a docking station where the waste in the waste reservoir may be removed.

15. The cleaning apparatus according to claim 1, the housing comprising floor bearing assemblies, each of the floor bearing assemblies having a floor engaging portion, further comprising one or more UV lights operable to wash one or more of the floor engaging portions of the floor bearing assemblies with UV light to thereby clean the one or more floor engaging portions.

* * * * *